US00PP15070P3

(12) United States Plant Patent
Montesino

(10) Patent No.: US PP15,070 P2
(45) Date of Patent: Aug. 3, 2004

(54) SHRUB ROSE PLANT NAMED 'RADCON'

(50) Latin Name: *Rosa hybrida*
Varietal Denomination: Radcon

(75) Inventor: Israel Montesino, Wilmington, DE (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 10/335,865

(22) Filed: Jan. 3, 2003

(65) Prior Publication Data

US 2004/0133952 P1 Jul. 8, 2004

(51) Int. Cl.[7] ..... A01H 5/00

(52) U.S. Cl. ..... Plt./107
(58) Field of Search ..... Plt./107

*Primary Examiner*—Anne Marie Grunberg
*Assistant Examiner*—Annette H Para
(74) *Attorney, Agent, or Firm*—Burns, Doane, Swecker & Mathis, L.L.P.

(57) ABSTRACT

A new and distinct variety of landscape shrub rose plant is provided which forms in abundance on a substantially continuous basis attractive single blossoms that are pink in coloration. The new variety is a spontaneous mutation of unknown causation of the 'Radrazz' variety (U.S. Plant Pat. No. 11,836) that forms vivid red single blossoms. The vegetation is vigorous and the growth habit is compact and mounding. Attractive ornamental satiny green foliage is formed. Excellent disease resistance to blackspot is exhibited. The new variety is particularly well suited for growing as distinctive ornamentation in the landscape.

1 Drawing Sheet

Botanical/commercial classification: *Rosa hybrida*/Shrub Rose Plant.
Varietal denomination: cv. 'Radcon'.

SUMMARY OF THE INVENTION

The new variety of *Rosa hybrida* landscape shrub rose plant of the present invention was discovered during March, 2001 while growing among a block of rose plants of the 'Radrazz' variety (U.S. Plant Pat. No. 11,836) growing in a nursery setting at West Grove, Pa., U.S.A. I was attracted to the new variety primarily because of its distinctive pink blossom coloration that was unlike that of the parental variety. The new variety is believed to be a spontaneous naturally-occurring mutation of the 'Radrazz' variety of unknown causation. Had I not discovered and preserved the original plant of the new variety it would have been lost to mankind.

It was found that the new variety of landscape shrub rose plant of the present invention possesses the following combination of characteristics:

(a) abundantly and substantially continuously forms attractive single blossoms that are pink in coloration unlike the vivid red blossoms of the 'Radrazz' variety (U.S. Plant Pat. No. 11,836), (b) exhibits a compact and mounding growth habit, (c) forms vigorous vegetation, (d) forms attractive ornamental green foliage with a satiny finish, and (e) exhibits excellent resistance to blackspot.

The new rose variety has attractive pink blooms, combined with a propensity for everblooming and blackspot resistance. The blooming cycle corresponds closely to that of the 'Radrazz' parental variety.

The new variety of the present invention can be readily distinguished from the parental 'Radrazz' variety through an inspection of the blossoms. More specifically, the new variety displays single blossoms that are pink in coloration rather than vivid red as are displayed by the 'Radrazz' variety. Also, the new variety of the present invention readily can be distinguished from the 'Radyod' variety (U.S. Plant patent application Ser. No. 10/336,811, filed Jan. 6, 2003). More specifically the blossoms of the 'Radyod' variety are a considerably lighter pink than those of the present variety.

The new variety well meets the needs of the horticultural industry. It can be grown to advantage as attractive ornamentation in parks, gardens, public areas, and residential landscapes. Accordingly, it is particularly well suited for growing throughout the landscape. The pink blossoms contrast nicely with the satiny green foliage.

The characteristics of the new variety have been found at West Grove, Pa., U.S.A., and at Wasco, Calif., U.S.A., to be homogeneous and stable and are strictly transmissible by asexual propagation such as budding, grafting, and the use of cuttings from one generation to another.

The new variety has been named the 'Radcon' variety, and is being marketed under the PINK KNOCK OUT trademark.

BRIEF DESCRIPTION OF THE PHOTOGRAPH

The accompanying photograph shows, as nearly true as it is reasonably possible to make the same in a color illustration of this character, a typical specimen of the flower of the new variety as well as a typical specimen of the flower of the parental 'Radrazz' variety. The rose plant from which the flowers were obtained were approximately two years of age and were grown in the ground outdoors on their own roots during September at West Grove, Pa., U.S.A.

FIG. 1 illustrates specimens of open flowers—plan view—obverse—with the flower of the new 'Radcon' variety being displayed on the right and the flower of the 'Radrazz' variety being displayed on the left. Dimensions in centimeters are included at the bottom of the photograph.

DETAILED DESCRIPTION

The chart used in the identification of colors is that of The Royal Horticultural Society (R.H.S. Colour Chart). The description is based on approximately two year-old specimens of the new variety during September while grown in the ground outdoors on their own roots at West Grove, Pa., U.S.A.

Class: Landscape Shrub Rose.

Plant:

*Height.*—Approximately 50 to 75 cm on average at the end of the growing season.

*Width.*—Approximately 75 to 100 cm on average at the end of the growing season.

*Habit.*—Compact, round, and bushy.

Branches:

*Color.*—Young stems: near Yellow-Green Group 144C.

*Thorns.*—Length: commonly approximately 10 mm in length on average. Base: somewhat oval, approximately 5 mm in length on average and approximately 2 mm in width on average. Shape: substantially triangular when viewed from the side. Color: near Yellow-Green Group 145B.

Leaves:

*Leaflets.*—Number: 3, 5, and 7. Shape: ovate with a serrulate margin, rounded base, and acuminate tip. Size: approximately 7 cm in length on average. Serration: fine. Texture: smooth. Overall appearance: very dense, leathery, and medium green in coloration, with a light satiny finish on the ventral surface. Color (adult foliage): upper surface: Green Group 136B to Yellow-Green Group 147B. Petioles: typically approximately 21 mm in length on average, typically approximately 1.3 mm in diameter on average, glabrous on both surfaces, and near Yellow-Green Group 145A in coloration. Rachis: typically approximately 38 mm in length on average, approximately 1.1 mm in diameter on average, glabrous on both surfaces, and near Grey-Brown Group 199A in coloration. Stipules: typically approximately 14 mm in length on average, typically approximately 5 mm in width on average, glabrous on both surfaces, and near Yellow-Green Group 145A in coloration.

Inflorescence:

*Number of flowers.*—Commonly approximately 3 to 4 blooms on average in a cluster.

*Peduncle.*—Length: typically approximately 33 mm on average. Diameter: typically approximately 1.7 mm on average. Texture: typically covered with small spines. Color: near Yellow-Green Group 144B.

*Sepals.*—Length: typically approximately 24 to 27 mm on average. Width: typically approximately 5 to 6 mm at the widest point on average. Configuration: possess an acuminate tip with a few foliaceous appendages and a truncate base. Number: five. Texture: the upper surface commonly is covered with fine white hairs, and the under surface is covered with short rigid projections.

*Buds.*—Length: commonly approximately 15 to 20 mm. Diameter: commonly approximately 7 to 10 mm. Shape: ovate. Texture: surface is scabrous with short hard points. Color: near Yellow-Green Group 145A prior to opening of sepals.

*Flower.*—Form: single and informal. Diameter: approximately 6 cm. on average. Color (when blooming): upper surface: near Red Group 48D. Fragrance: faint. Petal form: wedge-shaped with a curled apex. Petal number: approximately 12 on average. Petal length: commonly approximately 40 to 43 mm on average. Petal width: commonly approximately 26 to 35 mm on average. Petal apex: notched as illustrated in FIG. 1. Petal base: commonly cuneate to narrowly cuneate. Petal texture: glabrous. Anthers: commonly approximately 1 to 1.4 mm in length, approximately 0.75 mm in width, and near Greyed-Orange Group 165B coloration. Pollen: near Greyed-Orange Group 163B in coloration. Filaments: commonly approximately 3 to 9 mm in length, near Red Group 49A at the base, and commonly fading to Red Group 36D towards the tip. Stigmas: typically approximately 0.6 mm in length, approximately 1 mm in width, and near Yellow-Orange Group 19B with small patches of Orange Group 29B in coloration. Styles: typically approximately 4.2 mm in length on average, and near Orange-Red Group 33A in coloration. Receptacle: when the flowers are fully open commonly approximately 6.8 to 7.1 mm in diameter, and approximately 5.9 to 6.1 mm in height. Lasting quality: commonly approximately two weeks on the plant. Petal drop: very good with the petals commonly dropping cleanly and freely.

Development:

*Vegetation.*—Vigorous and strong.

*Blossoming.*—Abundant and substantially continuous.

*Resistance to diseases.*—Excellent with respect to rose blackspot.

*Propensity to form hips.*—None observed to date.

I claim:

1. A new and distinct variety of landscape shrub rose plant characterized by the following combination of characteristics:

(a) abundantly and substantially continuously forms attractive single blossoms that are pink in coloration unlike the vivid red blossoms of the 'Radrazz' variety (U.S. Plant Pat. No. 11,836), (b) exhibits a compact and mounding growth habit, (c) forms vigorous vegetation, (d) forms attractive ornamental green foliage with a satiny finish, and (e) exhibits excellent resistance to blackspot;

substantially as herein shown and described.

* * * * *

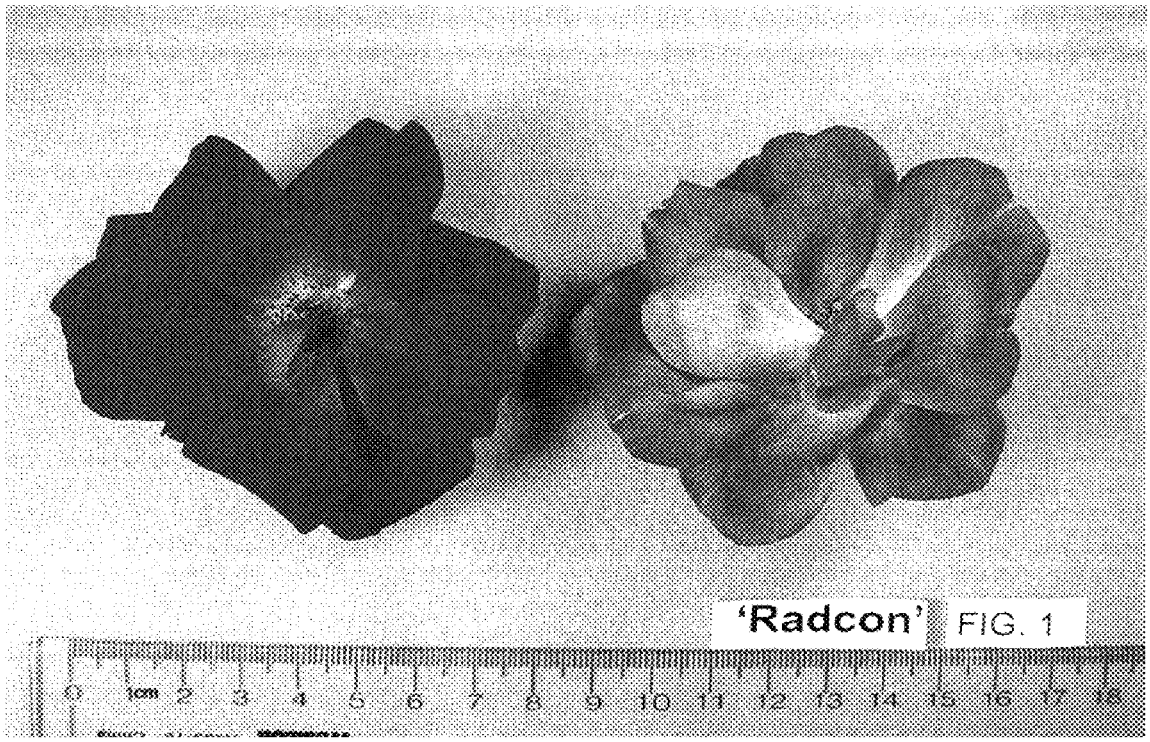
'Radcon' FIG. 1